United States Patent [19]

Mohr et al.

[11] Patent Number: 4,846,817
[45] Date of Patent: Jul. 11, 1989

[54] EXTERNAL URINARY DEVICE FOR WOMEN

[75] Inventors: Robert H. Mohr, Northville, Mich.; Barbara Pieper, 1356 Yorkshire, Grosse Pointe Park, Mich. 48230

[73] Assignees: Virginia Cleland, San Francisco, Calif.; Barbara Pieper, Gross Pointe Pk., Mich.

[21] Appl. No.: 73,757

[22] Filed: Jul. 14, 1987

Related U.S. Application Data

[63] Continuation-in-part of Ser. No. 886,979, Jul. 16, 1986, abandoned.

[51] Int. Cl.$^4$ .............................................. A61F 5/44
[52] U.S. Cl. ................................. 604/329; 604/331
[58] Field of Search ............... 604/327, 328, 329, 330, 604/331, 346–355; 128/760, 761, 767, 768, 769; 4/144.1–144.4

[56] References Cited

U.S. PATENT DOCUMENTS

| | | |
|---|---|---|
| 2,483,079 | 9/1949 | Williams . |
| 3,194,238 | 7/1965 | Breece . |
| 3,512,185 | 5/1970 | Ellis . |
| 3,583,388 | 6/1971 | Hovick . |
| 3,963,020 | 6/1976 | Hall . |
| 4,023,216 | 5/1977 | Rhea . |
| 4,484,917 | 11/1984 | Blackmon ............... 604/327 |
| 4,496,355 | 1/1985 | Hall et al. ............... 604/327 |
| 4,615,692 | 10/1986 | Giacalone et al. ....... 604/329 |
| 4,690,677 | 9/1987 | Erb ........................... 604/327 |

FOREIGN PATENT DOCUMENTS

| | | |
|---|---|---|
| 1004104 | 1/1977 | Canada ................... 604/ |
| 23942 | 2/1981 | European Pat. Off. ... 604/ |

Primary Examiner—C. Fred Rosenbaum
Assistant Examiner—Mario Costantino
Attorney, Agent, or Firm—Bielen and Peterson

[57] ABSTRACT

The invention provides a urinary device which can be used with comfort and safety when walking, as well as when sitting or reclining, and is characterized as comprising an externally applied support device, and a periurethral adapter which acts as an outflow tract or conduit, said device and adapter being interconnected so as to permit vertical or up and down adjustments of the adapter relative to the urinary meatus of the wearer and also permits in and out changes or adjustments in the position of the periurethral adapter, thus enabling the adapter to be positioned and maintained in contract with the urinary meatus. The periurethral adapter is characterized by a pair of laterally spaced flanges which lie between the labia minora, and in which the posterior vertically extending surfaces of the flanges which are received between the labia minora and engage the urinary meatus, are positioned to assist in preventing leakage. The previously mentioned vertical adjustment of the periurethral adapter is effected by providing the surface of the support device with a plurality of vertically spaced apertures into which the exit conduit may be selectively fitted and retained and in and out adjustment of the adapter are achieved by providing the body of the outflow tract with a series of corrugations spaced lengthwise of the body thereof, any of which may form a seal with the surrounding aperture in the support device. The periurethral adapter may be used alone without the support device by use of a suitable adhesive applied to the laterally spaced flanges and vertically extending surfaces therebetween.

15 Claims, 3 Drawing Sheets

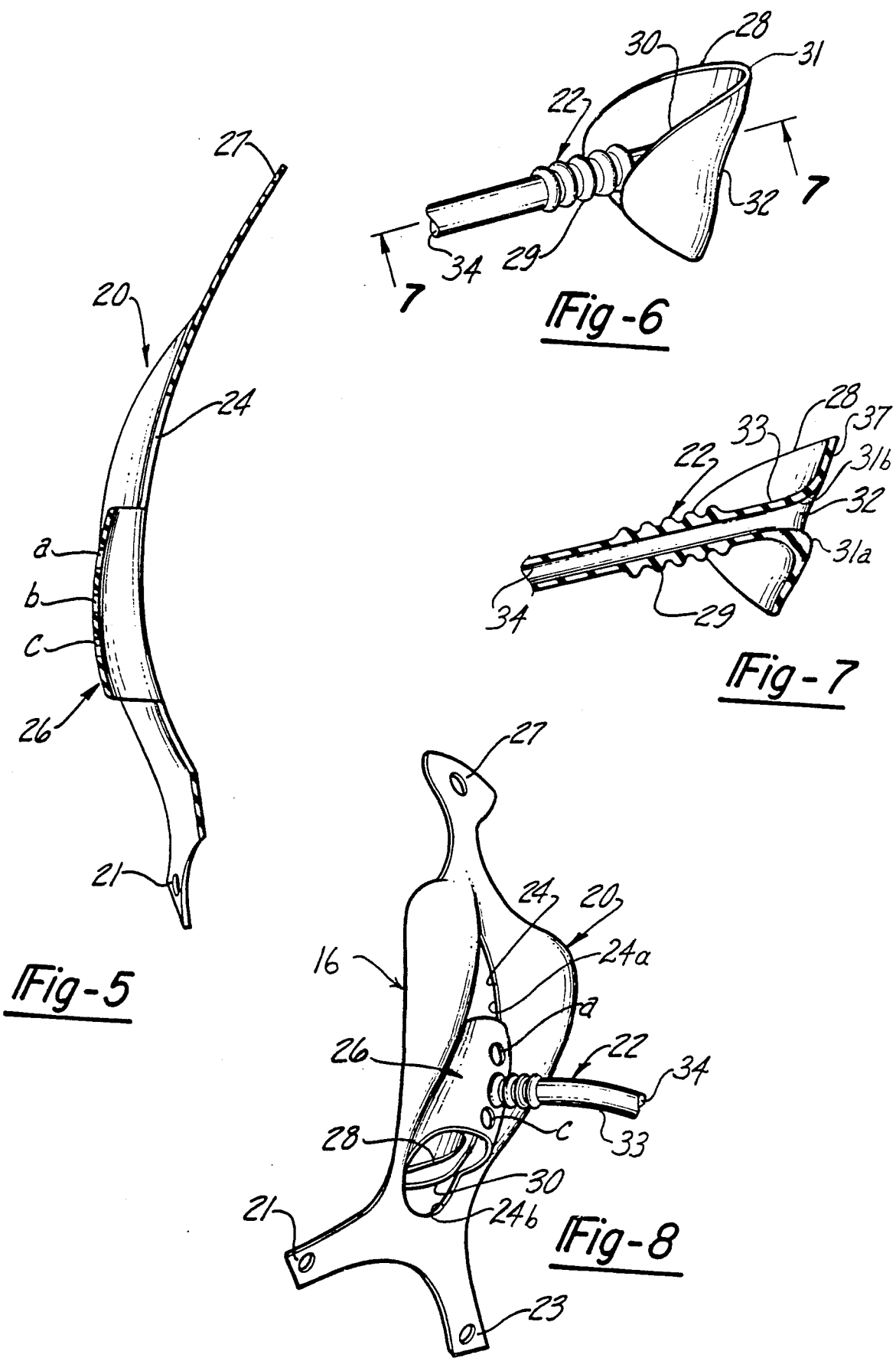

EXTERNAL URINARY DEVICE FOR WOMEN

BACKGROUND AND SUMMARY OF THE INVENTION

This application is a continuation-in-part of Application Ser. No. 886,979, filed July 16, 1986 now abandoned.

This invention relates to urinary devices and, more particularly, to a urinary device adapted for use by adult females who may be incontinent or have difficulty in controlling discharges from the bladder.

For a variety of neurological, physiological and/or anatomical reasons, many elderly women develop urinary incontinence. The causes are varied, but due to the health status of elderly women, surgical or medical treatment may be impossible and the incontinence becomes a health problem for these women.

Urinary incontinence is a condition characterized by involuntary loss of urine from the bladder in a degree which imposes a social hygienically unacceptable situation upon the person. Urinary incontinence is not a disease per se, but a symptom of a number of underlying conditions affecting the anatomy and innervation of the lower urinary tract. Estimates of the incidence of incontinence in hospitalized elderly patients ranges from 13 to 48 percent. Estimates of the incidence in elderly citizens living in the community range from 1.6 to 42 percent. Incontinence is a major reason for placing elderly in nursing homes. In fact, it has been estimated that 60 percent of elderly confined to institutions have no control of bladder functions. In addition to the patient factor, nursing care of the incontinent patient may take up to six times longer than care of the continent patient.

The impact of urinary incontinence on a woman's life may be a personal and social disaster. Many experience feelings of inferiority and inadequacy and often try to hide the problem by isolating themselves and avoiding socialization with others. Skin hygiene suffers and often skin eruptions, skin erosion, or decubitus ulcers form.

With the foregoing consideration in view, the principal objects of the present invention are to provide a urinary device which can be used with comfort and safety when walking as well as when sitting or reclining; to provide such a device which takes into consideration the dynamics of normal voiding, and also the fact that among normal women, there may be a substantial variation in the exact location of the external urethral orifice (urinary meatus) relative to the clitoris, vagina and labia.

Further objects of the present invention are to provide an external urine collection device for women, characterized as comprising an externally applied support device, and a periurethral adapter placed between the labia minora. The periurethral adapter also acts as an outflow tract or conduit.

Further objects are to provide such a device in which the support and adapter are interconnected so as to permit vertical or up and down adjustments of the periurethral adapter relative to the urinary meatus of the wearer and also permits relative in and out changes or adjustments in the position of the periurethral adapter, thus enabling the adapter to be positioned in contact with the urinary meatus; and to provide such a device in which the periurethral adapter is characterized by a pair of laterally spaced wings or flanges which lie between the labia minora, and which the posterior vertical surface between the lateral wings or flange is slightly extended and rounded at the point of contact beneath the urinary meatus to deter leakage.

Further objects of the invention are to provide a device as aforesaid in which the previously-mentioned vertical adjustment of the periurethral adapter is affected by providing the surface of the support device with plurality of vertically spaced apertures into which the exit conduit may be selectively fitted and retained; and provide such a device in which the aforesaid in and out adjustment of the adapter are achieved by providing the body of the outflow tract with a series of corrugations spaced lengthwise of the body thereof, any of which may form a seal with the surrounding aperture in the support device.

Further objects of this invention are to provide a periurethral adapter of the configuration described that is fabricated of a soft resilient substance in which the laterally spaced wings or flanges are thin and compliant, and to provide an adhesive to the surface of the adapter around the orifice of the outflow tract and over the surface of the flanges for connection of the adapter to a user without the use of the externally applied support device.

Other and more detailed objects of the present invention will appear in or be obvious from the following description of a preferred embodiment of the invention in which:

BRIEF DESCRIPTION OF THE DRAWINGS

FIG. 5 is a sectional view and partial elevation of the support device across line 5—5 in FIG. 2;

FIG. 6 is a perspective view of the periurethral adapter without the support device;

FIG. 7 is a cross sectional view of the adapter taken along line 7—7 of FIG. 6;

FIG. 8 is a front view in perspective of the support device and periurethral adapter in assembled relation to each other;

DETAILED DESCRIPTION OF THE PREFERRED EMBODIMENT

Figure 1:
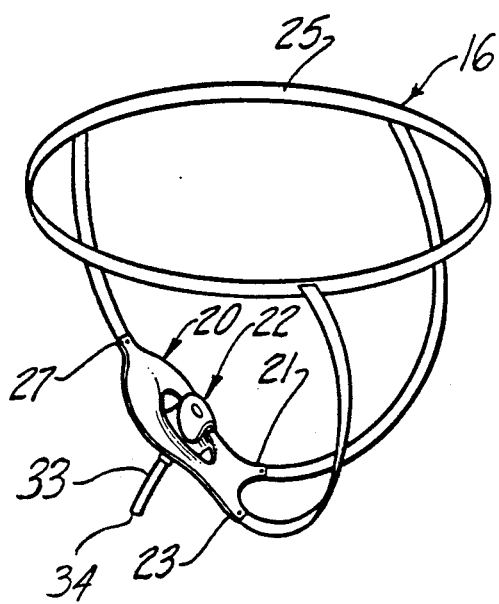
FIG. 1 is a perspective view illustrating the relation of the assembled support device and adapter to the anterior (single) and posterior (double) connections of usual support harness.
Figure 3:
FIG. 3 is a sectional view of the support device taken along the line 3—3 in FIG. 2.
Figure 4:
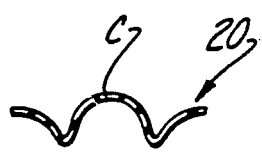
FIG. 4 is a sectional view of the support device across line 4—4 in FIG. 2.
Figure 2:
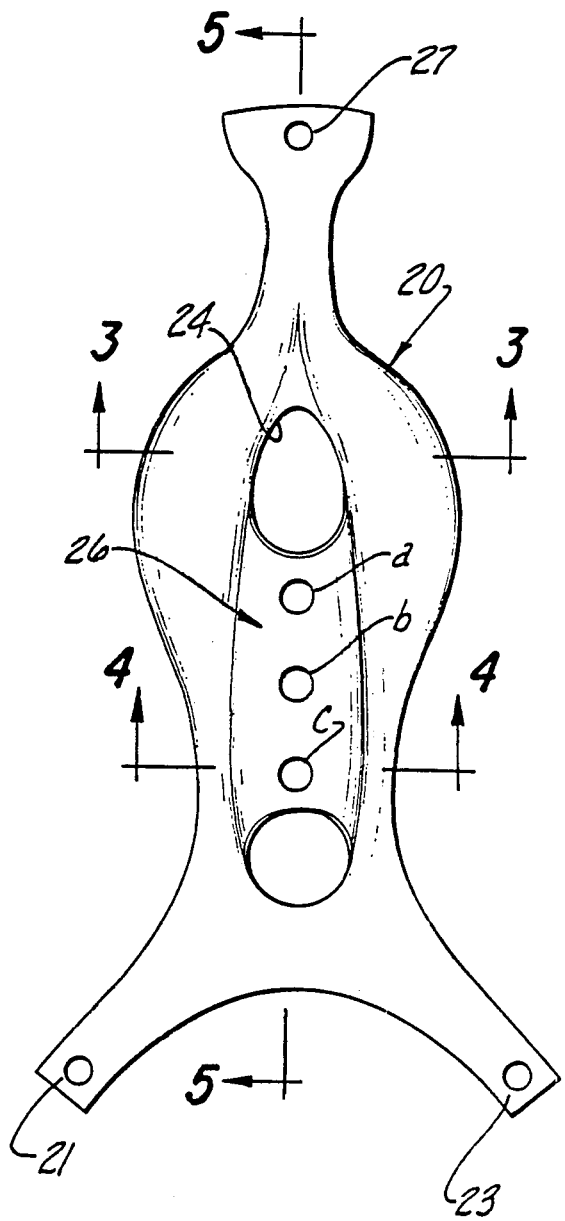
FIG. 2 is a separate view in front elevation of the support device of the invention without the periurethral adapter and without the harness attachment.

Referring now to FIGS. 1 through 11 of the drawings, the urinary device of the present invention is shown as a combined unit 16 in FIG. 1. The combined unit 16 comprises generally a support device 20, shown separately in FIGS. 2 through 5, and a periurethral adapter 22, the components whereof are shown in FIGS. 6, 7 and 8 for a first embodiment, and in FIGS. 9, 10 and 11 for a second embodiment.

The body 18 of the support 20 is quite flexible and is preformed or molded so that it causes the support to fit over and readily follow the contours of the labia majora of the wearer, as shown in FIGS. 2, 3, 4 and 5. It may be formed of any suitable impervious, pliant material selected for example from a variety of silicone rubber materials. The Medical Grade Elastomer known as Dow Corning MDX 44210 has been found to be satisfactory when reinforced with nylon or dacron mesh material.

The preformed support device 20 is retained in position generally aligned with and matching the contours of the labia majora by means of a usual harness 25 having two posterior tabs 21 and 23, provided with usual snap fasteners attached to the posterior straps of the harness 25. A single anterior tab 27 is snapped to the anterior harness snap and is preferably adjustable so that the wearer can control the placement of the support relative to the labia majora.

The support device 20 is provided with an enlarged vertically extending central opening 24, the elongated portion which is occupied by a bridge 26 of somewhat heavier section than the body 18, and is in turn provided with three vertically spaced apertures a, b and c. The tubular body 34 of the hereinafter described periurethral adapted 22, or the subsequently described alternate embodiment 36, can be selectively inserted through apertures a, b and c in order to provide three vertically spaced separately adjustable positions for the device relative to the urinary meatus. At its upper end 24a the opening 24 exposes the labia minora. At its lower end 24b, it exposes the vaginal opening. The arched bridge 26 helps position the body 18 of the support securely and comfortably upon the wearer.

Referring now to FIGS. 7 and 8, the periurethral adapter 22 is of elongated tubular form, and has a series of cylindrical corrugations 29 distributed along the proximal end thereof which serve, with the previously-mentioned apertures a, b and c, as positioning corrugations. The adapter 22 has a tubular body 33 that flares to a saddle section 35 that carries a pair of reversely turned identical wings or flanges 28 and 30 which are spaced from the respective sides of the tubular body 33 and lie between and engage the respective labia minora. The distal discharge end 34 of adapter 22 may be arranged for connection to any suitable receptacle for receiving urine from the user. By way of example, the total length of the periurethral adapter may be approximately six inches.

As appears in FIG. 8, the adapter 22 can be assembled with the support 20 by projecting the latter from the inside through a selected opening a, b or c, to its operative position in which the U-shaped generally vertically extending inner end 31 of the adapter is pressed against the periurethral tissue at a position in which the adapter inlet 32 is positioned in line with the urinary meatus.

The lower portion 31a, approximately one-half, of the reversely turned end 31 in the saddle portion 35 of the adapter projects somewhat further from the inner end thereof than does the upper portion 31b thereof, in order to ensure that the adapter 22 is pressed against the urinary meatus and is effective to deter leakage. The protruding portion 31a is thickened slightly such that this portion is deformable, but not readily compliant, whereby the protruding portion 31a seats in an anatomical recess in the periurethral area below the meatus and locates the compliant, remaining contact face of the saddle section 35 against the periurethral tissue in proper position aligning the inlet 32 with the urinary meatus.

The reversely turned end portions 31a and b of the flanges may also be and preferably are slightly wider and thicker than adjacent portions of the wings, to help anchor the device in place against the meatus and also assist in preventing leakage. The wings 28 and 30 are particularly compliant in composition to readily conform to the configuration of the labia minora.

In the relaxed normal condition of the adapter, as shown in the drawings, the outwardly and downwardly turned flanges are positioned at respectively opposite sides of the tubular body 33 and are received between the respectively opposite sides of and engage the labia minora of the user. The flanges are quite compliant and relatively thin and enable the device to adapt to the surrounding tissue. This enables the device to be used with comfort when walking as well as when sitting or reclining. By way of example, the material from which the flanges are formed may be selected from any of a variety of medical grade materials which will adhere to an adhesive, including latex or vinyl materials. The flanges when coated with an adhesive and adhered to the labia minora conform in configuration to the labia minora.

Depending upon the weight of the female, and upon other anatomical variations, the ends of the wings or flanges may extend out over the labia majora and be held in place by support 20 when the support 16 used in conjunction with the adapter. It may be desirable to trim back the marginal edges of the flanges flush with labia to improve the fit of the device particularly when used alone to inhibit inadvertent dislodgement.

In the positioning of the parts in the combination unit, the pressure of the inner end of the adapter against the periurethral tissue is determined by the selection of the corrugations carried by the adapter. Similarly, in this positioning cf the parts, the desired alignment in a vertical direction between the exit 34 in the adpater and the urethra is determined by the selection as between openings a, b and c.

Both the saddle 26 associated with the support 20 and the body of the adapter tube 33 may be formed of the previously mentioned well known materials. Preferably the material of one or both thereof should be slightly resilient in order to enable the corrugations on the adapter tube 33 to be snugly received between any two selected pairs of corrugations 29. Materials suitable for use in manufacturing the saddle 26 and the adapter tube include, for example, silicone rubber, urethane or latex.

In order to help hold the device in proper position, particularly when the adapter is used without the support, and also to prevent urine leakage it is preferred to apply any one of the conventional medical adhesives to the outer surfaces of the wings or flanges 28 and 30 and around the reversely turned end portions 31 a and b of the inner end of the adapter The perimeter 37 of the adapter 22 around the adapter inlet 32, except the lower portion 31a of the inner end 31, is structurally pliant to conform to the anatomical contours of the user, not only for comfort but to insure that a proper seal is maintained. The flanges 28 and 30 are particularly compliant to insure that the flanges conform to the delicate surface contour of the labia minora, rather than the labia minora being urged to conform to the configuration of the flanges.

In this manner stresses on the seal caused by normal movement of the patient are substantially reduced.

Figure 9:
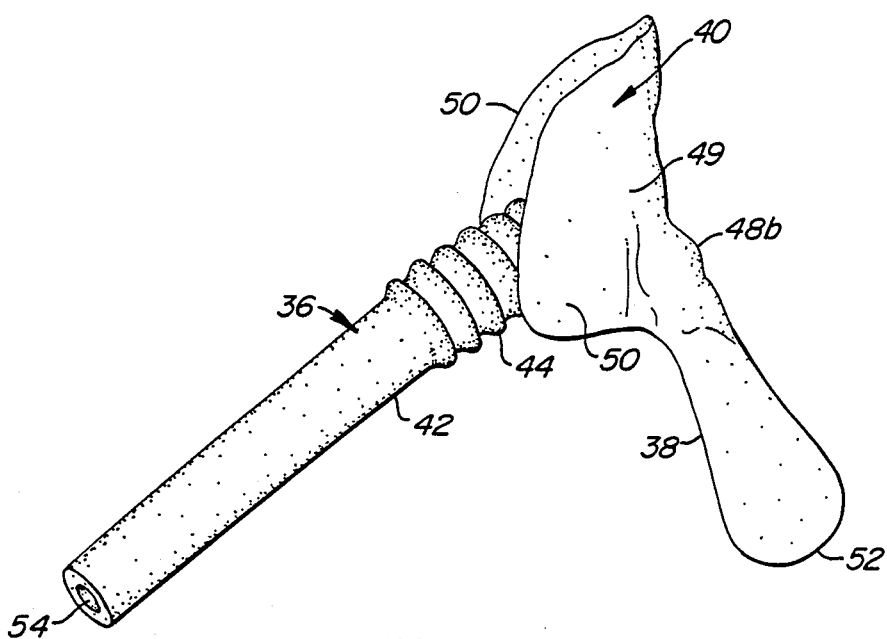
FIG. 9 is a perspective view of an alternate embodiment of the periurethral adapter.
Figure 10:
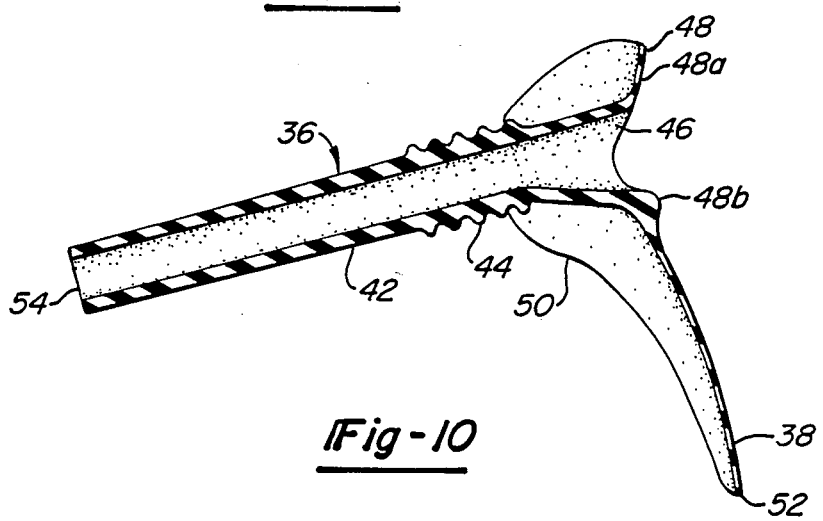
FIG. 10 is a cross sectional view of the adapter of FIG. 9.
Figure 11:
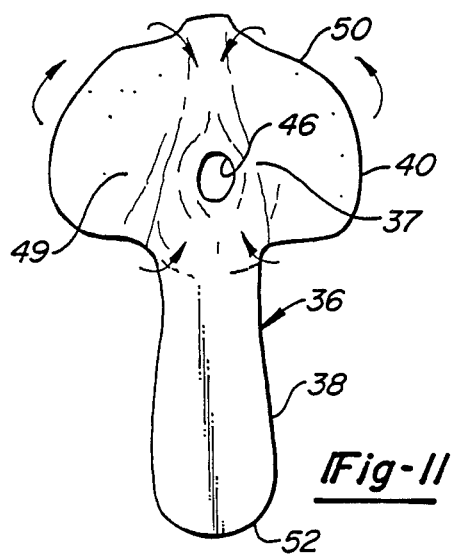
FIG. 11 is a front elevational view of the adapter of FIG. 9.

Referring to FIGS. 9, 10 and 11 an alternate embodiment of the periurethral adapter is shown. The modified adapter 36 includes an extension tab 38 to the saddle section 40 of the adapter for improved sealing and removal.

The adapter 36 is otherwise similar in construction and configuration to the previously described adapter 22. The adapter 36 includes a tubular body 42 with corregations 44 for coupling with the support device 20 of FIG. 2. The tubular body 42 flares at its inlet 46 to the saddle section 40 formed with an upper portion 48a and a protruding lower portion 48b of an inner end 48 that has turned back wings of flanges 50. The flanges, as in the previously described embodiment, are thin and of compliant composition to conform to the contour of the labia minora of the user.

The protruding portion 48b is thickened slightly such that this portion is deformable, but not readily compliant, whereby the protruding portion 48b seats in an anatomical recess in the periurethral area below the meatus and locates the compliant remaining contact face of the saddle section 40 against the periurethral tissue in proper position aligning the inlet 46 with the urinary meatus. The extension tab 38 is similarly constructed having a tapering thickness from the portion 48b of the inner end 48 proximate the inlet 46 to the distal tip 52.

When the adapter 36 is used without the support, an adhesive is applied to the contact face 49 of the saddle section 40 including the flanges 50 and the perimeter of the inner end 48 around the inlet. With an adhesive, the adapter is fabricated from a material such as medical grade latex, to which a benign adhesive such as adhesives marketed under the names Hollihesive or 3 m 1509 will adhere.

The vulva is washed and dried, the labia minora are spread and the adapter pressed against the urinary meatus with the inlet 46 aligned with the urethra. After holding the adapter in place for a few seconds with the flanges in contact with the inner surface o the labia minora, the adhesive forms a seal and retains the adapter in place. The soft tab 38 is tucked into the vagina and provides an extending shield for the section around the inlet most likely to become inadvertently detached, as well as a convenient tab to initiate peeling of the saddle section from the sensitive skin of the user during removal.

It has been found that the light weight and compliant construction of the adapter allows the adapter to be used without the support, which improves comfort. For such use, the discharge opening 54 is connected to a tube o collection (not shown) that is self supported to prevent additional tension or stresses from being placed on the adapter that would tend to break the seal.

It has been found that the adapter when properly adhered to the patient can be worn for repeated periods exceeding eight hours at a time. This provides not only a degree of comfort and confidence to bed ridden patients, but allows ambulatory patients a freedom not otherwise enjoyed.

It will be understood that various modifications of the construction of the present device and of the components thereof may be made within the spirit of the invention and that all such modifications and changes that come within the scope of the appended claims are embraced thereby.

What is claimed is:

1. A urinary device for a female comprising:

a base support formed of a pliant elastomer and means for securing the same in a predetermined position in contact with the labia majora area of female user, the surface of said support facing said area having an elongated apertured section with a centerline and a plurality of spaced apertures extending therethrough along the centerline, and a combined periurethral adapter releasably secured to said support, said adapter having a proximal end with an inlet portion constructed for contact with the urinary meatus of the user, a distal end for discharge of fluid and a tubular body between said proximal and distal ends serving as an flow circuit and being releasably received in any one of said apertures in the surface of the support, the said proximal end of said adapter being shaped to seat against the periutheral tissue of the user and inhibit the escape of urine from the urinary meatus and being formed with a pair of reversely turned outwardly and downwardly extending, laterally spaced compliant flanges which in relaxed condition of said adapter, are positioned at respectively opposite sides of said tubular body and are receivable between and engageable with the respective opposite sides of the labia minora, said flanges being relatively thin, and compliant wherein the adapter is of a unitary molded rubber-like composition with the tubular body including said proximal and distal ends having a relatively thick deformable construction that tapers from the inlet portion to the relatively thin, compliant flanges, the flanges being conformable to the contour of the labia minora, whereby the device can be used with comfort and safety when walking as well as when sitting or reclining.

2. The invention of claim 1 in which said base support is so constructed with an oval contoured configuration with a central arched bridge and arrangeable as to freely assume a position and configuration which approximates the configuration of the labia majora area of the user.

3. The structure of claim 2 in which said apertured section has a thickened portion about said apertures to give additional support to the connection between the support and the adapter member.

4. The structure of claim 2 in which the proximal end of the adapter which seats against the periurethral tissue has the adapter inlet portion positionable at the urinary meatus of the user and a thickened, extended portion engageable in an anatomical recess in the periurethral area below the meatus of the user, which extended portion applies pressure to the tissue and inhibits leakage when the adapter is seated against the periurethral tissue of the user.

5. The structure of claim 2 in which the proximal end of the adapter is formed as a pair of reversely turned flanges which are received between the labia, minora, and in which the surfaces of the flanges which are engageable with the labia minora of the user include a suitable medical adhesive when the proximal end of the adapter is seated against the periurethral tissue of the user.

6. The structure of claim 1 in which said apertured section has a thickened portion about said apertures to give additional support to the connection between the support and the adapter member.

7. The structure of claim 1 in which the proximal end of the adapter which seats against the periurethral tissue has the adapter inlet portion positionable at the urinary meatus of the user and a thickened, extended portion engageable in an anatomical recess in the periurethral area below the meatus of the user, which extended portion applies pressure to the tissue and inhibits leakage when the adapter is seated against the periurethral tissue of the user.

8. The structure of claim 1 in which the surfaces of the flanges which are engageable with the labia minora of the user include a suitable medical adhesive when the proximal end of the adapter is seated against the periurethral tissue of the user to improve sealing for inhibiting escape of urine.

9. A urinary device for a female comprising:
a base support formed of a pliant elastomer and means for securing the same in a predetermined position with respect to the labia majora of the user;
a combined periurethral adapter releasably secured to said support;
said adapter having a proximal end with an inlet portion constructed for contact with the urinary meatus of the user, a distal end for discharge of fluid and a tubular body between said proximal and distal ends serving as an flow circuit and being releasably supported by said base support;
said proximal end of the adapter being shaped to seat against the periurethral tissue of the user and inhibit the escape of urine from the urinary meatus and being formed with a pair of reversely turned outwardly and downwardly extending, laterally spaced compliant flanges which in relaxed condition of said adapter, are positioned at respectively opposite sides of said tubular body and are receivable between and in engagement with the respective opposite sides of the labia minora of the user, said flanges being relatively thin and compliant wherein the adapter is of a unitary molded rubber-like composition with the tubular body including said proximal and distal ends having a relatively thick deformable construction that tapers from the inlet portion to the relatively thin, compliant flanges, the flanges being conformable to the contour of the labia minora, whereby the device can be used with comfort and safety when walking as well as when sitting or reclining.

10. The structure of claim 9 in which the proximal end of the adapter which seats against the periurethral tissue has the adapter inlet portion positionable at the urinary meatus of the user and a thickened, extended portion engageable in an anatomical recess in the periurethral area below the meatus of the user, which extended portion applies pressure to the tissue and inhibits leakage when the adapter is seated against the periurethral tissue of the user.

11. The structure of claim 9 in which the surfaces of the flanges which are engageable with the labia minora of the user include a suitable medical adhesive when the proximal end of the adapter is seated against the periurethral tissue of the user.

12. A urinary device for a female user comprising:
a periurethral adapter of a unitary molded rubber-like composition having a tubular body with displaced ends with a saddle section at one end and discharge orifice at the opposite end, the saddle section having an inlet with a thick deformable portion around the inlet and turned back flanges with peripheral edges arranged on either side of the inlet, the flanges being of a thin tapered construction tapering from the thick deformable portion around the inlet to a thin portion around the peripheral edges, the flanges having the characteristic of being compliant, wherein said saddle section is constructed and configured with a contact face for contact with the urinary meatus of the user, the flanges being receivable between and conformable to the contour of the labia minora wherein the contact face of the adapter has a thin layer of adhesive and is attachable to a user by means of the adhesive on the contact face of the saddle section.

13. The device of claim 12 wherein the deformable portion of the saddle section is formed in a u-shape with the inlet centrally located on the deformable portion and alignable with the urinary meatus on placement of the contact face against the periurethral tissue between the labia minora of a user.

14. The device of claim 13 wherein the deformable portion has a lower part below the inlet the protrudes and seats in an anatomical recess below the urinary meatus of the user and positions the adapter.

15. The device of claim 14 wherein the lower part is thickened and less deformable than the remaining portion of the saddle section.

* * * * *